United States Patent [19]

Mackles et al.

[11] Patent Number: 5,405,603
[45] Date of Patent: Apr. 11, 1995

[54] MONOPHASIC AQUEOUS COMPOSITIONS CONTAINING AROMATIC LIPOPHILES

[76] Inventors: Leonard Mackles, 311 E. 23rd St., New York, N.Y. 10010; Leonard Chavkin, R.R. 1, Box 90, Bloomsbury, N.J. 08804

[21] Appl. No.: 177,068

[22] Filed: Jan. 3, 1994

[51] Int. Cl.$^6$ .......................... A61K 7/16; A61K 7/26
[52] U.S. Cl. ........................ 424/49; 424/58; 426/651
[58] Field of Search ...................... 424/49–58; 426/651

[56] References Cited

FOREIGN PATENT DOCUMENTS 2190405 2/1974 France .
2552992 4/1985 France .

*Primary Examiner*—Shep K. Rose
*Attorney, Agent, or Firm*—Omri M. Behr; Matthew J. McDonald

[57] ABSTRACT

A monophasic colorless transparent liquid aqueous composition substantially free from ethanol, comprising 0.05 to 2% by weight of one or more aromatic lipophiles; 0.05 to 2% by weight of the components of a salt of a divalent cation, $M(RSO_4)_2$, where M is a divalent cation selected from the group consisting of zinc and magnesium, and R is selected from the group consisting of $C_8$ to $C_{20}$ alkyl groups; and water to 100%, provided the ratio of the combined weights of the components of the divalent cation salt $M(RSO_4)_2$ to the weight of said one or more aromatic lipophiles is from 1:1 to 2:1. There is also provided a method for solubilizing one or more aromatic lipophiles in an aqueous suspension.

17 Claims, No Drawings

MONOPHASIC AQUEOUS COMPOSITIONS CONTAINING AROMATIC LIPOPHILES

BACKGROUND OF THE INVENTION

This disclosure concerns a novel composition and method for the solubilization of aromatic lipophiles in water.

Aromatic lipophiles are important ingredients in flavoring many aqueous-based products, such as mouthwashes; at levels as low as 0.1% by weight, they are able to impart a fresh pleasing flavor. However, these aromatic oils are difficult to solubilize in aqueous compositions at levels of 0.2% or greater. Given their hydrophobicity, they tend to remain in a phase separate from the aqueous phase, and so detract from the clear, transparent appearance of a monophasic aqueous composition.

Several conventional solutions to this solubilization problem have been proposed. The first of these is the inclusion of co-solvents, most commonly ethyl alcohol. Conventional mouthwashes commonly have to 10 to 30% by weight of ethanol. Although this is a high level of co-solvent for solubilizing an agent present at only 0.1-1%, ethyl alcohol serves several other functions besides solubilizing flavoring agents. For example, it acts as a cleanser, a surface tension lowering agent, a wetting and penetrating agent, and assists antimicrobial activity of any antiseptic ingredients present in the mouthwash.

Despite these multiple beneficial effects, recent epidemiological studies have reported that ethanol in mouthwashes, especially at higher concentrations, has been implicated in causing oral cancer and in poisoning very young children. Therefore, it is now desirable to omit ethanol or minimize its amounts in mouthwash.

Co-solvent alternatives to ethanol are few in number, especially if the product is one to be ingested. Suitable co-solvents for products to be ingested are limited to glycerine, propylene glycol and other glycols, suitably at levels of 5-30% by weight. As with ethanol, this is a rather high level to effect solubilization of oils present only at 0.2 to 1% by weight. A further drawback is that at levels of 5-30%, glycerine, propylene glycol and other glycols often impart an unpleasant taste to a composition.

Other co-solvents which have conventionally been employed are hydrophilic nonionic surfactants. One such surfactant is a polyethoxylated sorbitan ester (Tweens made by ICI Americas, Inc.). Solubilization of one part of peppermint oil in an aqueous composition requires five (5) parts Tween 80 (polyoxyethylene sorbitan monooleate). In other words, solubilization of 0.5% of an aromatic oil in water requires at least 2.5% by weight Tweens. At these levels, nonionic surfactants impart an undesirably bitter and soapy flavor to the aqueous composition. A further undesirable effect accompanying this level of nonionic surfactant is the reduction of antimicrobial activity of phenolic preservative, commonly present in mouthwashes.

In order to overcome the problem of the bitter, soapy flavor, a nonionic surfactant which has no taste has been proposed for solubilizing aromatic oils. This suffactant, polyoxyethylene-polyoxypropylene block copolymer (Pluronic 127, made by BASF Corporation)imparts no undesirable taste to the product. However, a substantially higher level of this surfactant is required to solubilize the oil than of Tweens: 1 part of aromatic oil in water requires at least 7 parts of this nonionic to effect solubilization. Although tasteless, these nonionic surfactants are thus not efficient solubilizers. Moreover, they share the undesirable side effect with Tweens of inactiveting phenolic germicides such as thymol.

All of the nonionic surfactants conventionally used have a further shortcoming: unlike ethanol, which significantly lowers surface tension, the nonionic surfactants have very little effect on surface tension. In summary, the nonionic surfactant co-solvents do not solubilize as well as ethanol and suffer significant undesirable secondary properties.

Anionic surfactants have also been explored as co-solvents for solubilizing aromatic oils in aqueous compositions. If used at concentrations greater than 0.3% by weight in mouthwashes, anionic surfactants are able to impart a very silky mouth feel to the product. Thus for example, sodium lauryl sulfate has been used alone or in combination with nonionic surfactants as described above. However, anionic surfactants impart a very bitter taste to the aqueous composition and irritate mucous membranes. Moreover, while sodium lauryl sulfate is able to solubilize aromatic oils at levels somewhat lower than nonionic surfactants (3 parts of sodium layryl sulfate to solubilize 1 part of a aromatic oil), an aqueous composition containing 0.2% of oil still requires at least 0.6% of sodium lauryl sulfate for solubilization. These strongly undesirable effects render anionic surfactants unsatisfactory as a co-solvent.

In U.S. Pat. No. 4,150,151, problems associated with mouthwash clarity were addressed by including 5-20% ethanol and 0.1-0.6% of a particular alkyl sulfate anionic surfactant mixture along with 0.1-2% of an essential oil as flavorant. The surfactant mixture consisted essentially of dodecyl (or lauryl) and tetradecyl surfactant salts in a weight ratio of 4:1 to 1:1. The cationic moiety could be chosen from, among others, $Na^{1+}$, $K^{1+}$, $Mg^{2+}$ or $NH_4^+$, or mixtures thereof, in a water carrier. The composition optionally further included a nonionic emulsifier, and, if desired, 0-2% of an alkali metal halide. The 4:1 to 1:1 ratio of lauryl to tetradecyl was said to be critical to keep the composition "water clear," i.e., free of clouding precipitate after storage at or below 35° F. for extended periods of time. Alternatively, for compositions not to be subjected to cold temperatures, the weight ratio of lauryl to tetradecyl surfactant salts could be 75:1 to 1:1.

U.S. Pat. No. 4,150,151 does not teach or suggest a desirable ratio of magnesium and halide ions (in equivalent amounts to each other) to be provided in a particular ratio to alkali metal ions with alkyl sulfate ions (again in equivalent amounts to each other). The term "equivalent" as used herein has the standard chemical meaning.

SUMMARY OF THE INVENTION

There is provided a monophasic colorless transparent liquid aqueous composition substantially free from ethanol comprising 0.05 to 2% by weight of one or more aromatic lipophiles; 0.05 to 2% by weight of the components of a salt of a divalent cation, $M(RSO_4)_2$, where M is a divalent cation selected from the group consisting of zinc and magnesium, and R is selected from the group consisting of $C_8$ to $C_{20}$ alkyl groups; and water to 100%, provided the ratio of the combined weights of the components of the divalent cation salt $M(RSO_4)_2$ to the weight of said one or more aromatic lipophiles is from 1:1 to 2:1.

There is also provided in a second embodiment a similar composition substantially free from ethanol comprising a monophasic colorless transparent liquid aqueous composition comprising 0.05 to 2% by weight of one or more aromatic lipophiles; 0.05 to 2% by weight of the components of a salt of a divalent cation, $M(B)_x$, where M is a divalent cation selected from the group consisting of zinc and magnesium; B is a halide or sulfate; and x is 1 when B is sulfate and 2 when B is a halide; 0.05 to 2% by weight of the components of a salt of a monovalent cation, $Na(RSO_4)$, where R is selected from the group consisting of $C_8$ to $C_{20}$ alkyl groups; and water to 100%, provided the ratio of the combined weights of the components of $M(B)_x$ and $Na(RSO_4)$ to the weight of said one or more aromatic lipophiles is from 0.8:1 to 2:1, and the stoichiometric ratio of $\{(M^{2+})+(B)_x\}$ to $\{(Na^+)+(RSO_4^-)\}$ is between 3.5:1 and 8:1. It should be noted that the prior art does not suggest or teach such a stoichiometric ratio.

In this second embodiment, the weight of the components of $M(B)_x$ may suitably be substantially equal to those of $Na(RSO_4)$. Further, both compositions may suitably further comprise 5–25% by weight of a co-solvent selected from the group consisting of glycerine, propylene glycol and polyols. Still further, the ratio of the combined weights of the components of the divalent cation salt $M(RSO_4)_2$ to the weight of said one or more aromatic lipophiles may be from 1:1 to 1.5:1.

In a third embodiment, there is provided a method for solubilizing one or more aromatic lipophiles in an ethanol-free aqueous suspension to form a monophasic colorless transparent liquid composition, said method comprising the steps of: incorporating into said suspension a salt of a divalent cation, $M(RSO_4)_2$, where M is a divalent cation selected from the group consisting of zinc and magnesium, and R is selected from the group consisting of $C_8$ to $C_{20}$ alkyl groups; provided the weight ratio of $M(RSO_4)_2$ to said one or more aromatic lipophiles is from 1:1 to 2:1.

A fourth embodiment provides a further method of solubilizing one or more aromatic lipophiles in an ethanol-free aqueous suspension to form a monophasic colorless transparent liquid aqueous composition, said method comprising the steps of: combining, in said aqueous suspension, the components of a salt of a monovalent cation, $Na(RSO_4)$, with the components of a salt of a divalent cation, $M(B)_x$, where R is selected from the group consisting of $C_8$ to $C_{20}$ alkyl groups, M is a divalent cation selected from the group consisting of zinc and magnesium, B is a halide or sulfate, and x is 2 when B is a halide and 1 when B is sulfate, provided that the ratio of the combined weights of the components of $M(B)_2$ and $Na(RSO_4)$ to the weight of said one or more aromatic lipophiles is from 0.8:1 to 2:1 and the stoichiometric ratio of $\{(M^{2+})+(B)_x\}$ to $\{(Na^+)+(RSO_4^-)\}$ is between 3.5:1 and 8:1.

DESCRIPTION OF THE PREFERRED EMBODIMENTS

Applicants have discovered a composition and method for solubilizing aromatic oils in aqueous systems without the drawbacks of conventional systems. The aromatic oil is solubilized in the aqueous composition by a divalent cation salt and a surfactant anion present at only low levels. The resulting composition is monophasic and transparent, but contains no ethanol, has no unpleasant taste and does not irritate mucous membrane.

In a first embodiment, there is provided a monophasic colorless trans-parent liquid aqueous composition substantially free from ethanol comprising 0.05 to 2% by weight of one or more aromatic lipophiles; 0.05 to 2% by weight of the components of a salt of a divalent cation, $M(RSO_4)_2$, where M is a divalent cation selected from the group consisting of zinc and magnesium, and R is selected from the group consisting of $C_8$ to $C_{20}$ alkyl groups; and water to 100%, provided the ratio of the combined weights of the components of the divalent cation salt $M(RSO_4)_2$ to the weight of said one or more aromatic lipophiles is from 1:1 to 2:1.

Thus, Applicants' composition goes even beyond U.S. Pat. No. 4,150, 151 discussed above in resolving difficulties of solubilizing aromatic oils. That patent was said to succeed in formulating a water clear liquid by incorporating a particular surfactant mixture at 0.1–0.6% by weight. In Examples 17, 19 and 29, this anionic surfactant mixture included magnesium lauryl sulfate and magnesium tetradecyl sulfate in a ratio of 1:1 to 4:1. In Examples 17 and 19, this anionic surfactant mixture and the essential oil were present in amounts of 0.4:0.3 and 0.5:0.3. Nevertheless, the composition of U.S. Pat. No. 4,150,151 do not foreshadow the instant invention because its anionic surfactant was restricted to a very precise type; and the resulting aqueous composition included at least 5% of ethanol. By contrast, the instant invention succeeds in producing a monophasic transparent aqueous mouthwash with lower levels of anionic surfactant without the ethanol or the particular magnesium lauryl sulfate to magnesium tetradecyl sulfate ratio of U.S. Pat. No. 4, 150, 151.

The composition of the first embodiment solubilizes one or more aromatic oils by incorporating the oil(s) into an ethanol-free aqueous composition with $M(RSO_4)_2$ surfactant salt in which R is a $C_8$–$C_{20}$ alkyl group and the weight ratio of $M(RSO_4)_2$ to the aromatic oil(s) is from 1:1 to 2:1. Since the $Mg(RSO_4)_2$ will be partially dissociated in the aqueous composition, the weight ratio is more accurately expressed as a ratio between the combined weights of the components of $Mg(RSO_4)_2$ to the weight of the one or more aromatic oils. This ratio has a value of from 1:1 to 1:2, or alternatively, from 1:1 to 1.5:1.

The ratio of the combined weights of the components of the divalent cation salt $M(RSO_4)_2$ to the weight of the one or more aromatic lipophiles is an important aspect of this invention. If this ratio between the weights of the divalent cation salt's components and the aromatic lipophiles is less than 1:1, then solubilization is incomplete and the composition is not monophasic, colorless or transparent. By contrast, if the ratio is greater than 2:1, a monophasic transparent liquid is obtained; but the presence of the divalent cation salt components begins to become noticeable in the taste of the composition. Therefore, the maximum level desirable of said divalent cation salt components in the composition is two times the weight of the aromatic lipophile.

Suitably, the R group of $Mg(RSO_4)_2$ in the ethanol-free composition may be predominantly a $C_{12}$ alkyl, making $RSO_4^-$ a lauryl sulfate group. Since M may be magnesium, one suitable $M(RSO_4)_2$ is magnesium lauryl sulfate, commercially available as "ELFAN 240" from Akzo Chemical Co.

Aromatic lipophiles which are suitable for solubilization in this composition include peppermint oil, thymol, menthol, eucalyptol and methyl salicylate.

It is noted that the composition may further incorporate from 5-25% by weight of a co-solvent. Suitable co-solvents include glycerine, propylene glycol and polyols. The presence of one or more of said co-solvents may lower the amount of divalent cation salt components required for solubilization of the aromatic lipophile. Accordingly, when said co-solvent is present, generally the ratio of the combined weights of the components of the divalent cation salt to the weight of said one or more aromatic lipophiles may be at from approximately 1:1 to 1.5:1.

In a second embodiment, there is also provided a similar composition substantially free from ethanol comprising a monophasic colorless transparent liquid aqueous composition comprising 0.05 to 2% by weight of one or more aromatic lipophiles; 0.05 to 2% by weight of the components of a salt of a divalent cation, $M(B)_x$, where M is a divalent cation selected from the group consisting of zinc and magnesium, B is a halide or sulfate, and x is 1 when B is sulfate and 2 when B is a halide; 0.05 to 2% by weight of the components of a salt of a monovalent cation, $Na(RSO_4)$, where R is selected from the group consisting of $C_8$ to $C_{20}$ alkyl groups; and water to 100%, provided the ratio of the combined weights of the components of $M(B)_2$ and $Na(RSO_4)$ to the weight of said one or more aromatic lipophiles is from 0.8:1 to 2:1, and the stoichiometric ratio of $\{(M^{2+})+(B)_x\}$ to $\{(Na^+)+(RSO_4^-)\}$ is between 3.5:1 to 8:1.

In this second embodiment of the invention, two salts which are slightly more readily available from commercial sources than $M(RSO_4)_2$, are added to the composition. These two salts, $M(B)_x$ and $Na(RSO_4)$, still solubilize aromatic oils in the aqueous composition.

The composition of this embodiment is a monophasic composition when two conditions are met. The first of these is that the ratio of the combined weights of the two salts' components to the aromatic oils is from 0.8:1 to 2:1. This ratio is distinguished from that in the first embodiment in that less of the combined weights of both salt components is required for solubilization. It is not clear why the lower endpoint of the ratio range may be lower than when $M(RSO_4)_2$ is added directly in the first embodiment. As in the first embodiment, the two salts in this embodiment dissociate to some degree into their ionic components once added to water, and reassociate to some degree either as the original salts or as variants thereof, e.g., $M(RSO_4)_2$ and NaB. This embodiment therefore appears to produce the $M(RSO_4)_2$ of the first embodiment in situ. Without in any way limiting the invention, it is Applicants' belief that this formation of magnesium lauryl sulfate in situ, combined with what is believed to be a "salting in" effect by both the monovalent and divalent salt components, is responsible for solubilizing the aromatic oil. In fact, these phenomena are believed to solubilize the aromatic oils even when the ratio of the salt components to that of the aromatic oil is lower than the 1:1 minimum ratio value in the first embodiment. Whether or not these phenomena do permit the solubilization at the lower ratio value, it is clear that the level of salt components' weight to the of the aromatic oil may be reduced in this second embodiment to a minimum level of 0.8:1.

The second condition needed for solubilization is that the stoichiometric ratio of the components of the two original salts $\{(M^{2+})+(B)_x\}$ to $\{(Na^+)+(RSO_4^-)\}$—i.e., the ratio of equivalents of $\{(M^{2+})+(B)_x\}$ to $\{(Na^+)+(RSO_4^-)\}$—be from 3.5:1 to 8:1. This stoichiometric ratio is based on the equation (where M is magnesium and B is Cl):

$$MgCl_2 + 2NaRSO_4 > Mg(RSO_4)_2 + 2NaCl.$$

It is surprising that the stoichiometric ratio range needed for solubilization should be as high as 3.5:1 to 8:1. The weight ratio between $M(RSO_4)_2$ and the aromatic oil makes the first embodiment's composition stable as a monophase. Thus, it might seem that to replace the $M(RSO_4)_2$ of the first embodiment with the two salts $M(B)_x$ and $NaRSO_4$ of the second, one would simply attempt to convert as much M in the $M(B)_x$ to $M(RSO_4)_2$ in the final composition as possible. One might be led to do this by adding at least two moles of $NaRSO_4$ for each mole of $M(B)_x$, so that each M cation would always have at least two $RSO_4^-$ anions with which to pair. In other words, one would attempt to maintain the stoichiometric ratio at a value of 1:1 or less.

However, it is unexpectedly found that the stoichiometric ratio range of $\{(M^{2+})+(B)_x\}$ to $\{(Na^+)+(RSO_4^-)\}$ which maintains the composition as a monophase is not a ratio of 1:1 or lower, corresponding to the molar ratio of $1M^{2+}:2(RSO_4^-)$ in $M(RSO_4)_2$. On the contrary, in order to maintain the composition in a monophase, there must 3.5 to 8 equivalents of $M(B)_x$ for each equivalent of $NaRSO_4$. It would appear that this ratio provides $M^{2+}$ cations in excess over the $RSO_4^-$ anions. Thus, at a stoichiometric ratio of 3.5: 1, there are provided 3.5 equivalents (or 1.75 moles) of $M^{2+}$) and 1 equivalent (or 1 mole) of $RSO_4^-$, leaving an apparent excess of 2.5 equivalents (or 1.25 moles) of $M^{2+}$; and at a ratio of 8:1, there are provided 8 equivalents (or 4 moles) of $M^{2+}$ to 1 equivalent (or 1 mole) of $RSO_4^-$, leaving an apparent excess of 7 equivalents (or 3.5 moles) of $M^{2+}$.

Besides having a surprisingly high value for the stoichiometric ratio, the instant invention is surprising in that the ethanol and the limited variety of C alkyl groups of U.S. Pat. No. 4,150, 151 need not be used.

In a third embodiment, there is provided a method for solubilizing one or more aromatic lipophiles in an aqueous suspension. This method comprises the steps of combining with said aromatic lipophiles in an aqueous suspension, a salt with a divalent cation $M(RSO_4)_2$ where M is a divalent cation of zinc or magnesium and R is selected from the group consisting of $C_8$ to $C_{20}$ alkyl groups, provided that the weight ratio of $M(RSO_4)_2$ to said one or more aromatic lipophiles is from 1:1 to 2:1.

The ingredients of the aqueous composition may be added in this method in any order, i.e., the aromatic lipophile need not be introduced into the water prior to the addition of the $M(RSO_4)_2$.

In yet another embodiment of the invention, there is provided a further method of solubilizing one or more aromatic lipophiles in an aqueous suspension. This further embodiment comprises the steps of: combining, in said aqueous suspension, the components of a salt of a monovalent cation, $NaRSO_4$, with the components of a salt of a divalent cation, $(M)(B)_x$, where R is selected from the group consisting of $C_8$ to $C_{20}$ alkyl groups, M is a divalent cation selected from the group consisting of zinc and magnesium, B is a halide or sulfate, and x is 2 when B is a halide and 1 when B is sulfate, such that the ratio of the combined weights of the components of $M(B)_x$ and $Na(RSO_4)$ to said one or more aromatic lipophiles is from 0.8:1 to 2:1 and the stoichiometric ratio of $\{(M^{2+})+(B)_x\}$ to $\{(Na^+)+(RSO_4^-)\}$ is between 3.5:1 and 8:1.

As in the preceding embodiment, the salt components and the one or more essential oils may be added in any order to the aqueous base.

While the present invention has been explained in relation to its preferred embodiments, it is to be understood that variations thereof will be apparent to those skilled in the art upon reading this specification. Thus, the present invention is intended to cover all variations which fall within the scope of the appended claims.

EXAMPLE I

In a stainless steel mixing vessel, 1 gram of oil of peppermint and 1.5 grams of magnesium lauryl sulfate are combined and in a sufficient amount of water to give a total of a 100 grams. This mixture is stirred at room temperature for 20 minutes. The resulting aqueous composition is monophasic, transparent and water-white.

EXAMPLE II

In a steel vessel, 2 grams of eucalyptol are combined 2 grams of magnesium chloride and 2 grams of sodium lauryl sulfate in a sufficient amount of water to give a total of 100 grams. This mixture is stirred for 15 minutes at room temperature. The resulting composition is monophasic, transparent and water-white.

EXAMPLE III 0.20 grams of natural peppermint oil was mixed with varying amounts of Tween 80 surfactant (polysorbate 80 from ICI Corp., a mixture of oleate esters of sorbitol and sorbitol anhydride consisting predominantly of the monoester condensed with 20 moles ethylene oxide) in a sufficient amount of water to give a total of 100 grams. The mixture was stirred until a clear solution was obtained. 1.00 gram of Tween 80 were required to effect solution at 15° C.

EXAMPLE IV 0.20 grams of natural peppermint oil was mixed with varying amounts of Pluronic 127 surfactant from BASF Corp., polyoxyethylene-polyoxypropylene block copolymer, conforming generally to the formula:

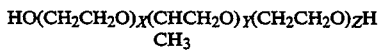
$$HO(CH_2CH_2O)_X(CHCH_2O)_Y(CH_2CH_2O)_ZH$$
$$CH_3$$

(in which the average values of X, Y and Z are 98, 67 and 98), and water to give a total of 100 grams. The mixture was stirred until a clear solution was obtained. 1.40 grams of Pluronic 127 were required to effect solution at 25° C.

EXAMPLE V 0.20 grams of natural peppermint oil was mixed with varying amounts of sodium lauryl sulfate surfactant in a sufficient amount of water to give a total of 100 grams. The mixture was stirred until a clear solution was obtained. 0.60 grams of sodium lauryl sulfate were required to effect solution at 25° C.

EXAMPLE VI 0.20 grams of natural peppermint oil was mixed with varying amounts of magnesium lauryl sulfate (ELFAN 240 from Akzo Corp.) and a sufficient amount of water to give a total of 100 grams. The mixture was stirred until a clear solution was obtained. 0.20 grams of magnesium lauryl sulfate were required to effect solution at 25° C.

EXAMPLE VII 0.20 grams of natural peppermint oil was mixed with varying amounts of sodium lauryl sulfate (USP Texapon LS 100 F from Henkel Corp.) and an equal weight of anhydrous magnesium sulfate in a sufficient amount of water to give a total of 100 grams. The mixture was stirred until a clear solution was obtained. 0.15 grams of each of sodium lauryl sulfate and magnesium sulfate were required to effect solutions at 25° C.

EXAMPLE VIII (in situ method)

0.20 grams of natural peppermint oil was mixed with varying amounts of sodium lauryl sulfate and an equal amount of zinc chloride in a sufficient amount of water to a total of 100 grams. The mixture was stirred until a clear solution was obtained. 0.10% of sodium lauryl sulfate and zinc chloride were required to effect solution at 25° C.

|  | Ex. III | Ex. IV | Ex. V | Ex. VI | Ex. VII | Ex. VIII |
|---|---|---|---|---|---|---|
| Tween 80 | 1.0 g | | | | | |
| Pluronic 127 | | 1.4 g | | | | |
| Sodium Lauryl Sulfate | | | 0.6 g | | | |
| Magnesium Lauryl Sulfate | | | | 0.2 g | | |
| Sodium Lauryl Sulfate | | | | | 0.15 g | |
| Magnesium Sulfate | | | | | 0.15 g | |
| Na Lauryl Sulfate | | | | | | 0.10 g |
| Zinc Chloride | | | | | | 0.10 g |

It can be seen from the above that the material needed to solubilize the peppermint oil in Examples VI through VIII is reduced significantly from the levels needed in Examples III through V. The solubilizers of Examples VI through VIII are 3-5 times more effective than the conventional solubilizers used in the compositions of Examples III–V.

Another series of experiments was undertaken to determine the solubilization effects of Applicants' system, using the following mixture of essential oils:

| Menthol | 16.0% |
|---|---|
| Eucalyptol | 36.0 |
| Methyl Salicylate | 24.0 |
| Thymol | 24.0 |
|  | 100.0% |

This mixture was used at a concentration of 0.25% by weight of the total composition in each of Examples IX through XIV with varying solubilizing materials in an amount of water sufficient to give a total amount of 100 grams. The amount of six different surfactants or salts which is required to solubilize the mixture of essential oils is shown in Examples IX through XIV.

|  | Ex. IX | Ex. X | Ex. XI | Ex. XII | Ex. XIII | Ex. XIV |
|---|---|---|---|---|---|---|
| Tween 80 | 1.2 g | | | | | |
| Pluronic 127 | | 1.5 g | | | | |
| Sodium Lauryl Sulfate | | | 0.7 g | | | |
| Magnesium Lauryl | | | | 0.3 g | | |

-continued

| | Ex. IX | Ex. X | Ex. XI | Ex. XII | Ex. XIII | Ex. XIV |
|---|---|---|---|---|---|---|
| Sulfate | | | | | | |
| Sodium Lauryl Sulfate | | | | 0.2 g | | |
| Magnesium Lauryl Sulfate | | | | 0.2 g | | |
| Sodium Lauryl Sulfate | | | | | 0.1 g | |
| Zinc Chloride | | | | | 0.1 g | |

Again, it can be seen from the above that the surfactant requirements needed to solubilize a mixture of essential oils are reduced significantly in the systems of Examples XII to XIV, which require only ½ to 1/6 the amount to effect solubilization as compared to those of Examples IX through XI of conventional solubilizers.

EXAMPLE XV 0.25 grams of the essential oil mixture used in Examples IX–XIV is combined with 99.35 grams water. 0.2 grams of sodium lauryl sulfate and 0.2 grams magnesium sulfate suffice to solubilize the essential oil. The ratio of the combined salt components to that of the oil is 0.4:0.25.

Similarly, 0.5 grams of essential oil is successfully solubilized by 0.4 grams sodium lauryl sulfate and 0.4 grams magnesium sulfate in 98.7 grams of water as is 1 gram oil mixture by 0.8 grams sodium lauryl sulfate and 0.8 grams magnesium sulfate in 97.4 grams of water. The constant ratio of (magnesium sulfate + sodium lauryl sulfate) to essential oil in these three mixtures which successfully solubilizes the oil mixture was 1.6:1.

EXAMPLE XVI 0.20 grams of the essential oil mixture used in Examples IX–XIV is combined with 10 grams of propylene gycol in a sufficient amount of water to make 100 grams. 0.15 grams of sodium lauryl sulfate and 0.15 grams of magnesium sulfate suffice to solubilize the essential oil. The ratio of the combined salt components to that of the oil is 1.5:1.

We claim:

1. A monophasic colorless transparent liquid aqueous composition substantially free from ethanol comprising
   a) 0.05 to 2% by weight of one or more aromatic lipophiles;
   b) 0.05 to 2% by weight of the components of a salt of a divalent cation, $(M)(RSO_4)_2$, where M is a divalent cation selected from the group consisting of zinc and magnesium, and R is selected from the group consisting of $C_8$ to $C_{20}$ alkyl groups; and
   c) water to 100%, provided the ratio of the combined weights of the components of the divalent cation salt $(M)(RSO_4)_2$ to the weight of said one or more aromatic lipophiles is from 1:1 to 2:1.

2. The composition according to claim 1 wherein said R is predominantly a $C_{12}$ alkyl.

3. The composition according to claim 1 wherein $RSO_4^-$ is lauryl sulfate.

4. The composition according to claim 3 wherein M is magnesium.

5. The composition according to claim 1 wherein said one or more aromatic lipophiles are selected from the group consisting of oil of peppermint, thymol, menthol, eucalyptol and methyl salicylate.

6. The composition according to claim 1 further comprising 5–25% by weight of a co-solvent selected from the group consisting of glycerine, propylene glycol and polyols.

7. The composition according to claim 1 comprising
   a) 0.2 to 1% by weight of said one or more aromatic lipophiles; and
   b) 0.25 to 1% by weight of said $M(RSO_4)_2$, said ratio of the combined weights of the components of the divalent cation salt $M(RSO_4)_2$ to the weight of said one or more aromatic lipophiles being 1:1 to 1.5:1.

8. A monophasic colorless transparent liquid aqueous composition substantially free from ethanol comprising
   a) 0.05 to 2% by weight of one or more aromatic lipophiles;
   b) 0.05 to 2% by weight of the components of a salt of a divalent cation, $M(B)_x$, where M is a divalent cation selected from the group consisting of zinc and magnesium; B is a halide or sulfate; and x is 1 when B is sulfate and 2 when B is a halide;
   c) 0.05 to 2% by weight of the components of a salt of a monovalent cation, $Na(RSO_4)$, where R is selected from the group consisting of $C_8$ to $C_{20}$ alkyl groups; and
   d) water to 100%, provided the ratio of the combined weights of the components of $M(B)_x$ and $Na(RSO_4)$ to the weight of said one or more aromatic lipophiles is from 0.8:1 to 2:1, and the stoichiometric ratio of $\{(M^{2+})+(B)_x\}$ to $\{(Na^+)+(RSO_4^-)\}$ is between 3.5:1 and 8:1.

9. The composition according to claim 8 wherein said R is predominantly a $C_{12}$ alkyl group.

10. The composition according to claim 8 wherein $RSO_4^-$ is lauryl sulfate.

11. The composition according to claim 10 wherein M is magnesium.

12. The composition according to claim 8 wherein said one or more aromatic lipophiles are selected from the group consisting of oil of peppermint, thymol, menthol, eucalyptol and methyl salicylate.

13. The composition according to claim 8 further comprising 25% by weight of a co-solvent selected from the group consisting of glycerine, propylene glycol and polyols.

14. The composition according to claim 8 wherein the weight of the components of $M(B)_x$ is substantially equal to those of $Na(RSO_4)$.

15. The composition according to claim 8 where M is magnesium and B is chloride or sulfate.

16. A method of solubilizing one or more aromatic lipophiles in an aqueous suspension to form a monophasic colorless transparent liquid aqueous composition, said composition being substantially free from ethanol, said method comprising incorporating into said suspension a salt of a divalent cation, $M(RSO_4)_2$, where M is a divalent cation selected from the group consisting of zinc and magnesium, and R is selected from the group consisting of $C_8$ to $C_{20}$ alkyl groups; provided the weight ratio of $M(RSO_4)_2$ to said one or more aromatic lipophiles is from 1:1 to 2:1.

17. A method of solubilizing one or more aromatic lipophiles in an aqueous suspension to form a monophasic colorless transparent liquid aqueous composition, said composition being substantially free from ethanol, comprising combining, in said aqueous suspension, the components of a salt of a monovalent cation, $Na(RSO_4)$, with the components of a salt of a divalent cation, $M(B)_x$, where R is selected from the group consisting of $C_8$ to $C_{20}$ alkyl groups;

M is a divalent cation selected from the group consisting of zinc and magnesium, B is a halide or sulfate; and x is 2 when B is a halide and 1 when B is sulfate, provided that the ratio of the combined weights of the components of $M(B)_2$ and $Na(RSO_4)$ to the weight of said one or more aromatic lipophiles is from 0.8:1 to 2:1, and the stoichiometric ratio of $\{(M^{2+})+(B)_x\}$ to $\{(Na^+)+(RSO_4^-)\}$ is between 3.5:1 and 8:1.

* * * * *